(12) United States Patent     (10) Patent No.: US 8,287,651 B2
Benson et al.     (45) Date of Patent: Oct. 16, 2012

(54) CELLULOSE PRETREATMENT PROCESS

(75) Inventors: Robert Benson, North Bay (CA); Chris Bradt, Lasalle (CA); Regis-Olivier Benech, Chatham (CA); Richard Romeo Lehoux, Windsor (CA)

(73) Assignee: GreenField Ethanol Inc., Toronto (CA)

( * ) Notice: Subject to any disclaimer, the term of this patent is extended or adjusted under 35 U.S.C. 154(b) by 302 days.

(21) Appl. No.: 12/560,843

(22) Filed: Sep. 16, 2009

(65) Prior Publication Data

US 2010/0065128 A1     Mar. 18, 2010

Related U.S. Application Data

(60) Provisional application No. 61/097,692, filed on Sep. 17, 2008.

(51) Int. Cl.
    *C13K 1/02* (2006.01)
(52) U.S. Cl. .................. 127/37; 162/14; 162/15; 162/21
(58) Field of Classification Search .................... 127/37; 162/14, 15, 21
See application file for complete search history.

(56) References Cited

U.S. PATENT DOCUMENTS

| | | | | |
|---|---|---|---|---|
| 3,939,286 | A * | 2/1976 | Jelks | 426/312 |
| 4,136,207 | A * | 1/1979 | Bender | 426/510 |
| 4,461,648 | A | 7/1984 | Foody | |
| 5,424,417 | A | 6/1995 | Torget et al. | |
| 5,628,830 | A | 5/1997 | Brink | |
| 6,090,595 | A | 7/2000 | Foody et al. | |
| 6,419,788 | B1 | 7/2002 | Wingerson | |
| 6,878,212 | B1 | 4/2005 | Pinatti et al. | |
| 7,815,741 | B2 * | 10/2010 | Olson | 127/1 |
| 2008/0044877 | A1 | 2/2008 | Penttila et al. | |
| 2009/0023187 | A1 | 1/2009 | Foody et al. | |
| 2009/0221814 | A1 | 9/2009 | Pschorn et al. | |
| 2010/0065128 | A1 | 3/2010 | Benson et al. | |

FOREIGN PATENT DOCUMENTS

| | | |
|---|---|---|
| CA | 2 464 090 A1 | 10/2001 |
| WO | 02/14598 A1 | 2/2002 |

OTHER PUBLICATIONS

MacMillian. 1996. Hemicellulose conversion to Ethanol. Handbook on bioethanol: production and utilization. C. Wyman, Editor, Taylor and Francis, Washington DC pp. 287-313.
Badal, C.S. 2003. Hemicellulsoe bioconversion. J. Ind. Microb. Biotechnol. 30/5:279-291.
Walther, T., P. Hensirisak, F.A. Agblevor. 2001. The influence of aeration and hemicellulose sugars on xylitol production by *Candida tropicalis*. Biores. Technol. 76/3: 213-220.
Clarke, A.J. 1996. Chemistry and structure of cellulose and heteroxylan. In Biodegradation of cellulose: Enzymology and Biotechnology. Lancaster, Pa: Technomic Press, pp. 9.
Torget, R., P. Walter, M. Himmel, K. Grohmann. 1991. Dilute-acid pretreatment of corn residues and short rotation woody crops. Appl. Biochem. Biotechnol. 28/29:75-86.
Torget, R., P. Walter, M. Himmel, K. Grohmann. 1992. Dilute-acid pretreatment of two short-rotation herbaceous crops. Appl. Biochem. Biotechnol. 34/35:115-123.
Rydholm, S.A. 1965. Wood chemistry. In Pulping processes. Interscience Publisher, NY. p. 95-96.
Ruzene, D.S., E. Yagiz, D. Marangoz, D.P. Silva, A.A. Vicente, J.A. Teixeira. 2008. Hydrothermal treatments of corn cobs and hemicellulose extraction. In Proceedings of the 10th International Chemical and Biological Engineering Conference, CHEMPOR 2008. E.C. Ferreira and M. Mota eds. Braga, Portugal, Sep. 4-6, 2008.
Garrote, G., H. Dominguez, J.C. Parajo. 1999. Mild autohydrolysis : an environmentally friendly technology for xylooligosaccharide from wood. J. Chem. Technol. Biotechnol. 74:1101-1109.
Vasquez, M.J. J.L. Alonso, H. Dominguez, J. C. Parajo. 2006. Enhancing the potential of oligosaccharides from corncob autohydrolysis as prebiotic food ingredient. Industrial Crops and products. 24:152-159.
Moura, P., R. Barata, F. Carvalheiro, F. Girio, M.C. Loureiro-Diaz, M.P. Esteves. 2007. In vitro fermentation of xylo-oligosaccharides from corn cobs autohydrolysis by Bifidobacterium and Lactobacillus strains. LWT. 40:963-972.
Garrote, G., H. Dominguez, J.C. Parajo. 2001. Kinetic modelling of corncob autohydrolysis. Proc. Biochem. 36: 571-578.
Garrote, G., H. Dominguez, J.C. Parajo. 2002. Autohydrolysis of corncob: study of non-isothermal operation for xylooligosaccharide production. J. Food. Eng. 52: 211-218.
Aoyama, M. 1996. Steaming pretreatment of bamboo grass. II. Characterization of solubilised hemicellulose and enzymatic digestibility of water extracted residue. Cellulose Chemistry and Technology. 30:385-393.
Carvalheiro. F., M.P. Esteves, J.C. Parajo, H. Peirera, F.M. Girio. 2004. Production of oligosaccharides by autohydrolysis of brewery's spent grain. Bioressource Technology. 91: 93-100.
Gans, I., D. Potts, A. Matsuo, T. Tse, M. Holysh, P. Assarsson. 1989. Process development for plug flow acid hydrolysis and conversion of lignocellulosics to ethanol. In Bioenergy: Proc 7th Can. Bioenergy R&D Semina, E. Hogan, ed., NRC Canada, pp. 419-423.

(Continued)

*Primary Examiner* — David M Brunsman
(74) *Attorney, Agent, or Firm* — Ladas & Parry LLP (57) ABSTRACT

A process for the production of ethanol from biomass is disclosed. The process relates to the pretreatment of corncob biomass and includes the steps of exposing corncob to steam in a reaction vessel at an elevated temperature and reaction pressure for a preselected exposure time. Volatile compounds are continuously vented during pretreatment. The reaction pressure is released for explosive decomposition of the corncob biomass into fibrous solids and condensate. The exposure is preferably carried out at a temperature of 190-210° C. and a pressure of 190 psig to 275 psig and an exposure time of 3 to 10 minutes.

10 Claims, 7 Drawing Sheets

OTHER PUBLICATIONS

Lawford, H.G., J.D. Rousseau. 1992. Effect of acetic acid on xylose conversion to ethanol by genetically engineered *E. coli*. Appl. Biochem. Biotechnol. 34/35:185-204.

Ferrari, M.D., E. Neirotti, C. Albornoz, E. Saucedo. 1992. Ethanol production from Eucalyptus wood hemicellulose hydrolyzate by *Pichia stipitis*. Biotech. Bioeng. 40:40753-759.

Lawford, H.G., J.D. Rousseau. 1993. Effect of pH and acetic acid on glucose and xylose metabolism by a genetically engineered ethanologenic *Escherichia coli*. Appl. Biochem. Biotechnol. 39/40:301-322.

McMillan, J.D. 1994. Conversion of hemicellulose hydrolyzates. In Bioconversion for fuels. M.E. Himmel, J.O. Baker and R.P. Overend, eds., ACS Symposium Seried 566, American chemical Society, pp. 411-437.

Narendranath, N.V. K.C. Thomas. W.M. Ingledew. 2001. Acetic acid and lactic acid inhibition of growth of *Saccharomyces cerevisiae* by different mechanisms. J. Am. Soc. Brew. Chem. 59:187.

Narendranath, N.V. K.C. Thomas. W.M. Ingledew. 2001. Effects of acetic acid and lactic acid on the growth of *Saccharomyces cerevisiae* in a minimal medium. Journal of industrial microbiology and Biotechnology. 26/3: 171-177.

Kuyper, M., A.A. Winkler, J.P. Van Dijken, J.T. Pronk. 2004. Minimal metabolic engineering of *Saccharomyces cerevisiae* of efficient anaerobic xylose fermentation: a proof of principle. FEMS Yeast Res. 4: 655-664.

Krisch, J., B. Scajani. 1997. Ethanol and acetic acid tolerance in free and immobilized cells of *Saccharomyces cerevisiae* and Acetobacter aceti. Biotechnology Letter. 19/6: 525-528.

Pampulha, M.E. and Loureiro-Dias, M.C. (1990) Activity of glycolytic enzymes of *Saccharomyces cerevisiae* in the presence of acetic acid. Appl. Microbiol. Biotechnol. 34/3:375-380.

Thomas, K. C. S. H. Hynes, W.M. Ingledew. 2002. Influence of medium buffering capacity on inhibition of *Saccharomyces cerevisiae* growth by acetic acid and lactic acids. Appl. Environ. Microbiol. 68/4:1616-1623.

Graves, T., N.V. Narendranath, K. Dawson, R. Power. 2006. Effects of lactic or acetic acid on ethanol productivity by *Saccharomyces cerevisiae* in corn mash. Appl. Microbiol. Biotechnol. 33/6:469-474.

* cited by examiner

Figure 1. Effect of sulphuric acid addition on pH of Miscanthus and corn cob prehydrolysates Figure 2. Conversion time of Miscanthus and corn cobs prehydrolysates Figure 3. Effect of cooking severity on xylose content Figure 4A. Effect of initial adjustment of pH on fermentation of corn cobs hydrolysate containing 0.6 % (w/v) acetic acid Figure 4B. Effect of initial adjustment of pH on fermentation of corn cobs hydrolysate containing 1.2 % (w/v) acetic acid Figure 5. Schematic of batch pretreatment process Figure 6. Effect of xylose content on hydrolysis

CELLULOSE PRETREATMENT PROCESS

CROSS REFERENCE TO RELATED APPLICATIONS

This application claims the benefit of priority of U.S. Provisional Patent Application No. 61/097,692 filed Sep. 17, 2008, the contents of which is incorporated herein by reference.

FIELD OF THE INVENTION

The invention relates to alternate fuels from biomass, in particular ethanol produced from biomass.

BACKGROUND OF THE INVENTION

Ethanol for fuel has become a significant part of the transportation fuel mix. This is due to the rapidly increasing price of fossil fuel and as the desire to reduce the environmental impact of non-renewable fuels.

Ethanol is a simple molecule, non-toxic and miscible with gasoline. When ethanol is made by the fermentation of plant derived starches and sugars, it is considered to have a lower environmental impact than fossil fuels.

Ethanol is usually produced from starch or sugar by fermentation. In North America the feedstock is primarily corn, while in Brazil sugar cane is used. There are disadvantages to using potential food or feed plants to produce ethanol and the availability of such feedstock is limited by the overall available area of suitable agricultural land.

Many alternate feedstocks for ethanol production have been proposed. Among them is lignocellulosic biomass. This term includes cellulose containing agricultural and wood residues, purpose grown non-food crops, and a wide variety of biodegradable wastes.

Agricultural and wood residues and non-food crops have several economic and environmental advantages over corn and starch. Furthermore, some alternative crops such as Miscanthus, Switchgrass and hybrid Poplar can even grow on poor quality land not suitable for corn. Wood and agricultural residues have relatively low market value and have the potential to be high volume feedstocks for ethanol production.

Lignocellulosic biomass is composed of three major polymers: cellulose, hemicellulose and lignin. Cellulose makes up 40% to 60% of lignocellulosic biomass and is the desired target for ethanol production. Cellulose resembles starch in many ways. It is a homogeneous polymer made of linked glucose monomers, as is starch. Cellulose, however, is much more difficult to depolymerize than starch. This is due to a difference in the nature of the glucose linkages as well as the presence of hemicellulose and lignin. As a result, more severe conditions are needed to hydrolyze cellulose to glucose than are needed to hydrolyze starch.

One process for converting lignocellulosics to ethanol can be called the enzymatic hydrolysis process. This process requires five major unit operations: feed preparation, pretreatment, enzymatic hydrolysis, fermentation and distillation. Lignocellulosic biomass is chopped, cleaned, and ground to the desired size.

Pretreatment of the biomass opens up its structure, exposing the cellulose to the hydrolytic action of enzymes in the hydrolysis step. Pretreatment also increases the concentration of cellulose in the prehydrolysate, which improves the digestibility of the cellulose by enzymes.

In the enzymatic hydrolysis step, the prehydrolysate obtained in the pretreatment step is cooled to about 40° C. to 60° C., cellulase enzymes are added and the hydrolysis is allowed to continue to achieve the desired conversion of cellulose to glucose. Fermentation of the sugars in the hydrolysate by yeast is the next step.

In the final step, ethanol is recovered by distillation of the fermented mash and dehydration of ethanol to the desired concentration. Many different configurations for this step are practiced in the industry.

Lignin is a potent inhibitor of hydrolysis and some soluble lignin derivatives inhibit the fermentation process. Thus, it is desirable to use a lignocellulosic feedstock which is low in lignin. The lignin content of corncobs, (less than 8% by weight) is low, which would make this a good biomass feedstock for the production of ethanol. However the hemicellulose content of corncobs is high, almost 30% of the total dry matter. Moreover, much of the hemicellulose is acetylated. The dissolution of hemicellulose leads to the formation of acetic acid, a powerful inhibitor of the yeast fermentation process used to produce ethanol. This is a problem, since the acid remains in the pretreated biomass and carries through to the hydrolysis and fermentation steps.

In known pretreatment processes, mineral acids such as sulfuric acid, are added to the biomass for hydrolysis of the biomass components. This approach is disadvantageous since large amounts of water are required to flush the acid from the pretreated cellulose prior to the enzymatic hydrolysis step. Moreover, acid pretreatment also leads to the dissolution of hemicellulose and the release of acetic acid, as discussed above. Many of the compounds released in the pretreatment step, such as acetic acid, hemicellulose and many hemicellulose degradation products are inhibitors of and retard the downstream fermentation process. This results in increased capital equipment costs and frequently incomplete conversion of the glucose to ethanol. Therefore, it would be desirable to reduce the hemicellulose content of the feedstock for the enzymatic hydrolysis step to aid in cellulose digestion.

In an alternate approach a steam gun cellulose pretreatment is used. Biomass ground to the desired size is subjected to steam under pressure and at elevated temperatures. The pressure is then released rapidly by way of a fast acting valve, leading to an explosion of the cooked biomass material. In this approach the steam explosion may be a batch process or a continuous process.

Hemicellulosic hydrolysate composition is highly dependent on feedstock type and pretreatment methodology. Significant compositional differences are observed among hemicellulosic biomasses. The hemicellulose polysaccharides are quite heterogeneous because they can contain hexoses, pentoses and organic acids e.g. acetic acid (1-3). Softwood xylan is weakly acetylated while hardwood xylan is highly acetylated (4). Acetic acid levels in hemicellulose hydrolysates of herbaceous species are approximately 50% lower than typically observed in similarly prepared hardwood hydrolysates because of the lower degree of hemicellulose acetylation in herbaceous species relative to hardwood (5, 6). Average values of acetyl content recorded in Table 1 show that some of the highest levels of hemicellulose acetylation are found in corn residues such as cornstalks and corn cobs (7-8).

TABLE 1

Acetyl content of lignocellulosic biomasses

| Sources | Acetyl (%, average) |
| --- | --- |
| Softwoods | 1.4 |
| Hardwoods | 3.7 |

TABLE 1-continued

Acetyl content of lignocellulosic biomasses

| Sources | Acetyl (%, average) |
|---|---|
| Grasses | 1.9 |
| Wheat straw | 2.9 |
| Corncobs | 3.1 |
| Cornstalks | 4.6 |

Extractive-Free Dry Basis Analysis

Figure 1:
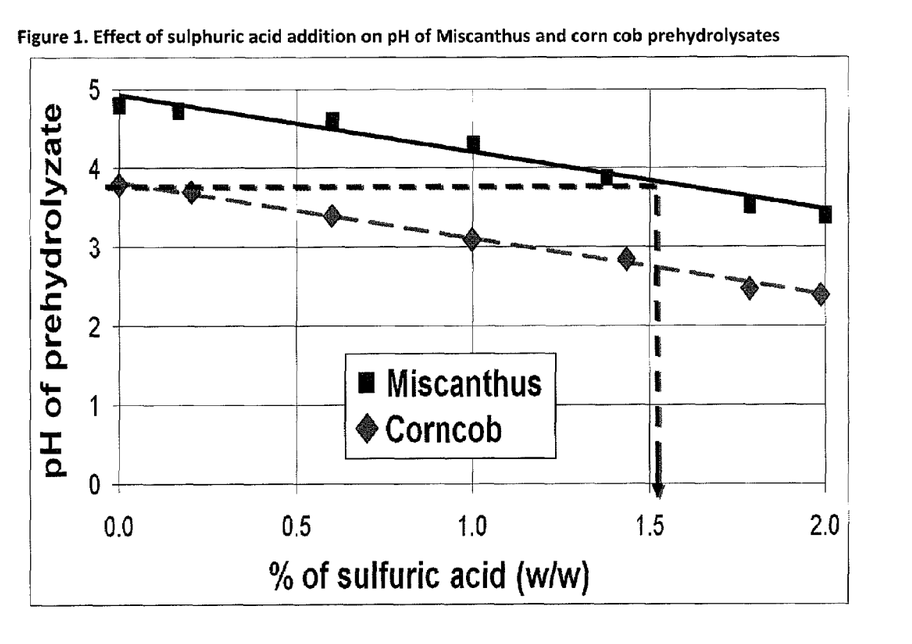
FIG. 1 shows the effect of acid addition on the pH of Miscanthus and corncobs

Pretreatment of highly acetylated lignocellulosic materials such as corn cobs can be performed in absence of mineral acids i.e. autohydrolysis (9-11). Our results showed that high temperature steam explosion pretreatment of corn cobs produces prehydrolysates with a pH that ranges from pH 3.5 to pH 3.8. Results plotted on FIG. 1 showed that, under similar pretreatment conditions, a dosage of 1.6% to 1.8% (w/w) of sulphuric acid is required to produce Miscanthus (grasses) prehydrolysate with the same pH values as corncob prehydrolysate.

High temperature steam pretreatment converts acetyl groups in hemicellulose molecules into acetic acid which then hydrolyses xylan polymer into xylose oligomers and monomers (12, 13). The formation rate and concentration of these compounds in the resulting prehydrolysates depend on the autohydrolysis conditions e.g. temperature and reaction time which can be controlled to produce the desired level of acetic acid and hemicellulose hydrolysis (12-15).

Figure 2:
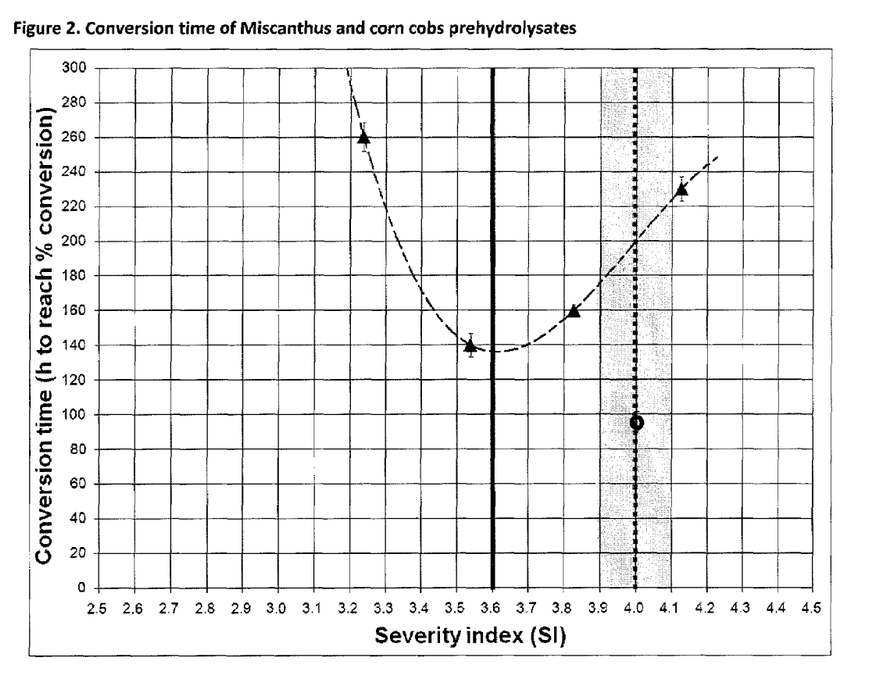
FIG. 2 shows the conversion time of corn cobs hydrolysate (circle, 95 h+/−5 h) produced under optimum conditions (grey box, SI: 3.88 to 4.11) and continuous or batch operation compared to conversion times of Miscanthus hydrolysates produced under a wide range of batch pretreatment severities i.e. combinations of pretreatment temperatures and times (triangle). The pH of corn cobs and Miscanthus steam exploded prehydrolysates was 3.8. Hydrolysis of corn cobs and Miscanthus prehydrolysates were carried out using similar conditions i.e. 20% consistency hydrolysis, 2.5% load of enzyme, pH 5.0, 50° C.

The acetic acid content of 20% consistency corn cobs hydrolysates produced under optimum pretreatment conditions ranges from 0.6% to 1.2% (w/v) after enzymatic hydrolysis. The content of acetic acid has to be controlled since it is considered as one of the dominant fermentation inhibitors in hydrolysates of hemicellulosic biomasses (16-23). The presence of acetic acid significantly reduces the performance of ethanologenic organisms. It inhibits fermentation in an exponential way (24). The mechanism of its toxicity involves the acidification of the cytoplasm and modification of certain enzymes of glycolysis (25). Steam explosion pretreatment trials carried out with other hemicellulose biomasses such as Miscanthus showed that the selected range of pretreatment severities is specific to corncobs (FIG. 2)

Figure 4A:
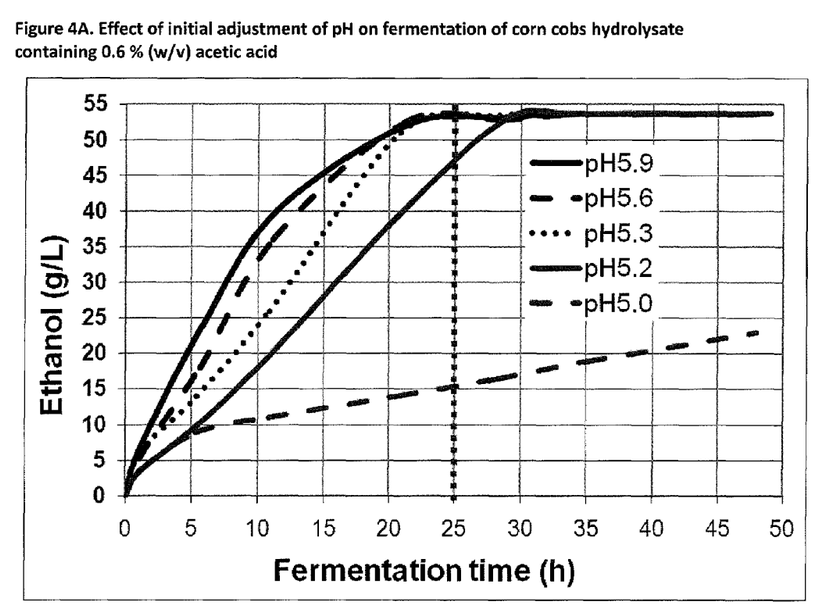
FIG. 4A shows the impact of initial pH adjustment on fermentation of corn cobs hydrolysate containing 0.6% (w/v) acetic acid.
Figure 4B:
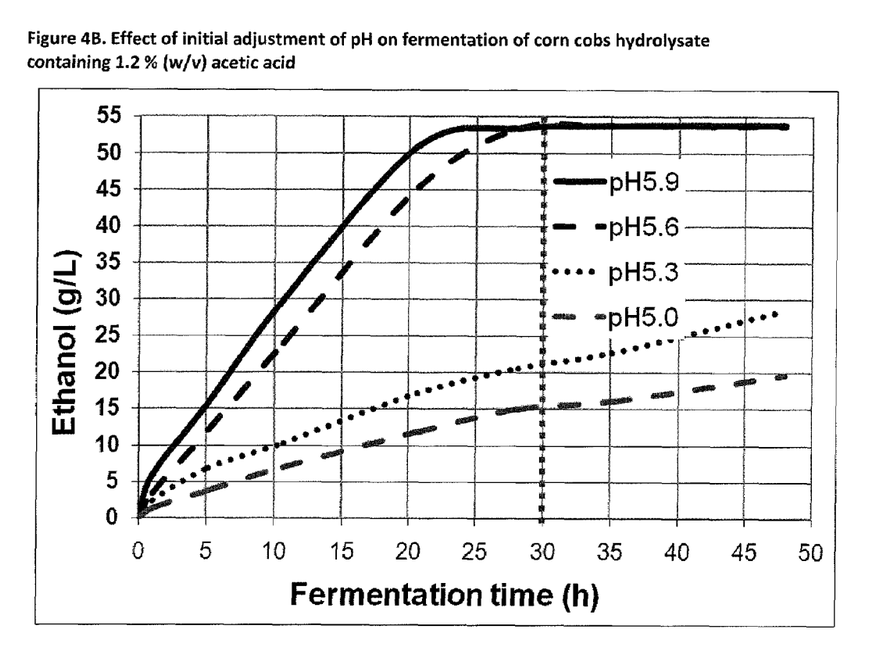
FIG. 4B shows the impact of initial pH adjustment on fermentation of corn cobs hydrolysate containing 1.2% (w/v) acetic acid.

Fermentation of 20% consistency corncobs hydrolysates produced under optimum conditions is shown in FIGS. 4A and 4B. 54 g/l of ethanol were produced in 25 h to 30 h at pH values that ranged from pH 5.3 to pH 5.9. This production of ethanol corresponded to 94% of the maximum theoretical glucose to ethanol conversion.

In the presence of 0.6% acetic acid, this ethanol production was reached in 25 h following an initial pH adjustment at pH values that ranged from pH 5.3 to pH 5.9, using 30% ammonium hydroxide (FIG. 4A). In the presence of 1.2% acetic acid, similar ethanol production was reached in 30 h following an initial pH adjustment at pH 5.6 (FIG. 4B).

These results are in accordance with results reported in the literature which showed that the tolerance to moderate acetic acid concentrations of the yeast *Saccharomyces cerevisiae* is strongly pH dependant. Carrying out fermentation of a complex medium at pH value higher than the pka of acetic acid (pKa 4.75) substantially reduces inhibition by acetic acid (21-27).

Foody in U.S. Pat. No. 4,461,648 describes a method of increasing the accessibility of cellulose in wood by steam explosion. However the authors state that a temperature of 205° C. for 15 minutes is required to achieve the maximum yield of glucose. The yield of glucose has a maximum of only 33%. An acid catalyst is needed.

U.S. Pat. No. 6,090,595 (Foody) teaches that the key to processing corncobs and other agricultural residues is to select the correct feedstock. No method of modifying the processing conditions to improve glucose yield is described. Pretreatment is carried out at pH 0.5 to 2.5.

Foody et al. in patent application US20090023187 focus on the separation of sugars by Simulated Moving Bed chromatography. Pretreatment is described as taking place at low pH.

Wingerson in U.S. Pat. No. 6,419,788 describes the pretreatment of biomass with oxygen at a pH of 8 to 13.

In each of these patents the conditions of pretreatment require extended treatment time or the use of chemicals to achieve acceptable recovery of glucose from lignocellulosic biomass.

SUMMARY OF THE INVENTION

It is now an object of the present invention to provide a process which overcomes at least one of the above disadvantages.

It is a further object to provide a cellulose pretreatment process wherein no mineral acid is added and the amount of acetic acid released in the pretreatment step is controlled to reduce the amount of acetic acid in the prehydrolysate.

The inventors have now surprisingly discovered that the use of a mineral acid in the pretreatment step can be avoided and the amount of acetic acid in the prehydrolysate reduced by closely controlling the treatment conditions during the pretreatment step. In particular, the conditions are chosen such that sufficient acetic acid is produced to pretreat the biomass by the process of autohydrolysis, while limiting the acetic acid content in the prehydrolysate to a level which does not cause any significant delays in the downstream fermentation process.

In one aspect, the invention provides a process for the pretreatment of corncob biomass, which includes the steps of exposing corncob to steam at elevated temperatures and pressure for a preselected amount of time, venting the volatiles continuously during pretreatment and releasing the pressure for explosive decomposition of the corncob biomass into fibrous solids and condensate, wherein the exposing step is carried out at a temperature of 195-215° C. and a pressure of 188 psig to 290 psig and the preselected time is 4 to 10 minutes. Preferably, the exposing step is carried out at a temperature of 203 to 207° C., most preferably 205° C., a pressure of 220 psig to 250 psig, most preferably 235 psig and for a treatment time of 7 to 9 minutes, most preferably 8 minutes. Volatile products of hemicellulose degradation (e.g. furfural, HMF and furans) are vented for the duration of the pretreatment to prevent the formation of carbon material. The pressure is preferably released within less than 100 milliseconds (ms), preferably within 60 ms, most preferably within 30 ms. The process preferably includes the further steps of separately capturing condensate and solids generated during cooking and pressure release and removing the captured condensate at the bottom of the reaction vessel prior to the pressure release. The corncob biomass is preferably chopped or ground prior to the exposure step to a particle size of 0.5 to 1 cm$^3$.

BRIEF DESCRIPTION OF THE DRAWINGS

Other objects and advantages of the invention will become apparent upon reading the detailed description and upon referring to the drawings in which:

FIG. 2.

DETAILED DESCRIPTION OF PREFERRED EMBODIMENTS

Before explaining the present invention in detail, it is to be understood that the invention is not limited to the preferred embodiments contained herein. The invention is capable of other embodiments and of being practiced or carried out in a variety of ways. It is to be understood that the phraseology and terminology employed herein are for the purpose of description and not of limitation.

The abbreviations used in the Figures have the following meaning:
T, temperature in ° C.
RT, retention time, min
DM, Dry matter
$t_{90\%}$, time (hours) to reach 90% of the maximum theoretical conversion of cellulose to glucose The invention is directed to ethanol from biomass processes and especially to cellulose pretreatment processes. In particular, the invention is directed to processes intended to reduce the amount of hemicellulose and acetic acid in the cellulose hydrolysis feed stream when cornbob is used as the starting material.

Hemicellulose is a heteropolymer or matrix polysaccharide present in almost all plant cell walls along with cellulose. While cellulose is crystalline, strong, and resistant to hydrolysis, hemicellulose has a random, amorphous structure with little strength. Hydrolysis of hemicellulose can be relatively easily achieved with acids or enzymes enzymes. Hemicellulose contains many different sugar monomers. For instance, besides glucose, hemicellulose can include xylose, mannose, galactose, rhamnose, and arabinose. Xylose is the monomer present in the largest amount.

While cellulose is highly desirable as a starting material for enzymatic ethanol production, hemicellulose and its hydrolytic degradation products interfere with the enzymatic hydrolysis of cellulose and the downstream fermentation of glucose from cellulose. Xylose derivatives and degradation products, and acetic acid, (all of which are products of hemicellulose hydrolysis), are inhibitors of glucose fermentation.

A preferred aspect of the invention is a process for the pretreatment of corncob biomass for generating a cellulose prehydrolysate with reduced acetic acid content compared to acid pretreatment processes. The preferred process of the invention includes the steps of exposing corncob to steam at elevated temperatures and pressure for a preselected exposure time, venting volatile compounds continuously during the pretreatment and releasing the pressure to achieve explosive decomposition of the corncob biomass into fibrous solids and condensate, wherein the exposing step is carried out at a temperature of 190-215° C. and a pressure of 188 psig to 290 psig and the preselected time is 3 to 10 minutes. Preferably, the exposing step is carried out at a temperature of 203 to 207° C., most preferably 205° C., a pressure of 220 psig to 250 psig, most preferably 235 psig and for a treatment time of 7 to 9 minutes, most preferably 8 minutes. The pressure is preferably released within less than 1000 milliseconds (ms), preferably within 600 ms, most preferably within 300 ms.

The condensate and solids generated during cooking and at pressure release are preferably separately captured. The condensate is collected at the bottom of the reaction vessel and removed through a drainage valve. The solids expelled from the reaction vessel upon pressure release, also referred to as prehydrolysate, are separated from the gaseous reaction products in a cyclone separator, collected at the bottom of the separator, and transported to the enzymatic hydrolysis step. The corncobs are preferably chopped or ground prior to the exposure step.

A series of test treatments of a feedstock such as corncobs were conducted to determine the process conditions determinative of acetic acid, hemicellulose and hemicellulose degradation products in the prehydrolysate. The effectiveness of each set of pretreatment conditions was determined by monitoring the time to reach various percentages of the theoretical maximum cellulose to glucose conversion. In order to compare overall cellulose digestibility, $t_{90\%}$ i.e. the time to reach 90% conversion was chosen. The feedstock was pretreated in a batch pretreatment by a steam gun process without the addition of any acid. Composition analysis was carried out at the analytical laboratory of Papriban (Montreal, Canada), using the TAPPI methods T249 cm-85 and Dairy one (wet chemistry analysis).

Batch pretreatment operating conditions were screened with respect to high cellulose to glucose conversion rates and low level of toxin generation. The pretreatment conditions were chosen to ensure sufficient acetic acid was released to pretreat the biomass by the process of autohydrolysis, while at the same time limiting the acetic acid content of the prehydrolysate obtained to a level which will not cause significant delays in the fermentation process. The treatment conditions were further chosen to optimally remove hemicellulose without generating excess acetic acid in order to minimize the hemicellulose content in the prehydrolysate obtained. Finally, the treatment conditions were adjusted to minimize the content in the prehydrolysate of hemicellulose degradation products which inhibit downstream fermentation. The overall hydrolysis and fermentation of the batch-pretreated corncobs was generally less than 120 hours.

Quantification of soluble products from pretreatment and enzymatic hydrolysis was carried out by HPLC analysis. Target molecules were monitored to determine the relative contents of cellulose and downstream inhibitors in the prehydrolysate obtained. The target molecules were sugar monomers such as glucose and xylose as well as toxic compounds such as different carboxylic acids, namely acetic acid, succinic acid and lactic acid and degradation products of carbohydrates such as glycerol, HMF and furfural.

The summary results of the test treatment series are plotted in FIGS. 1 to 4 and 6.

Figure 3:
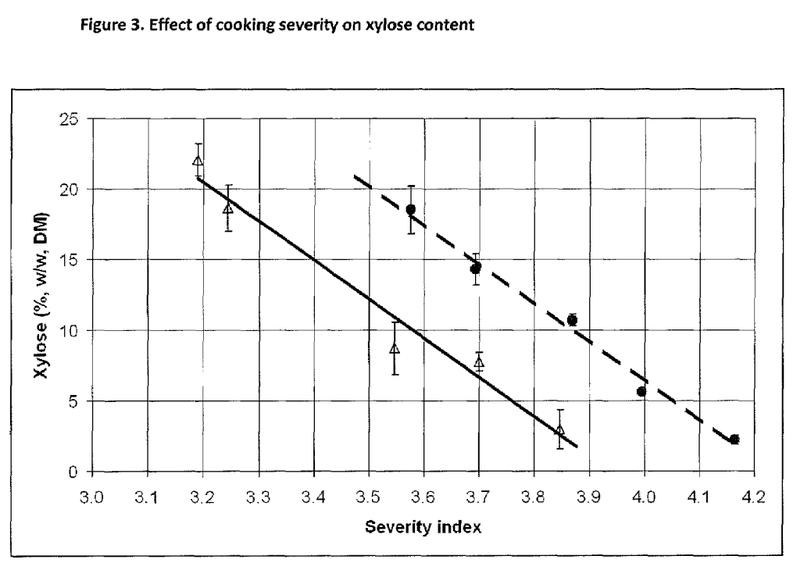
FIG. 3 shows the impact of various combinations of cooking time and temperature on the content of xylose remaining in corncob prehydrolysate fibers. The xylose content was measured on the total wet biomass and reported on a dry matter basis; Batch steam explosion: Circles and dashed line; Continuous steam explosion: triangle and plain line.

As shown in FIG. 3, steam explosion pretreatment led to a significant decrease in the amount of xylose remaining in the wet fibers of pretreated corncobs, compared to the content of insoluble xylose in untreated corncob, which was 24.5+/−0.6 (%, w/w DM).

Figure 6:
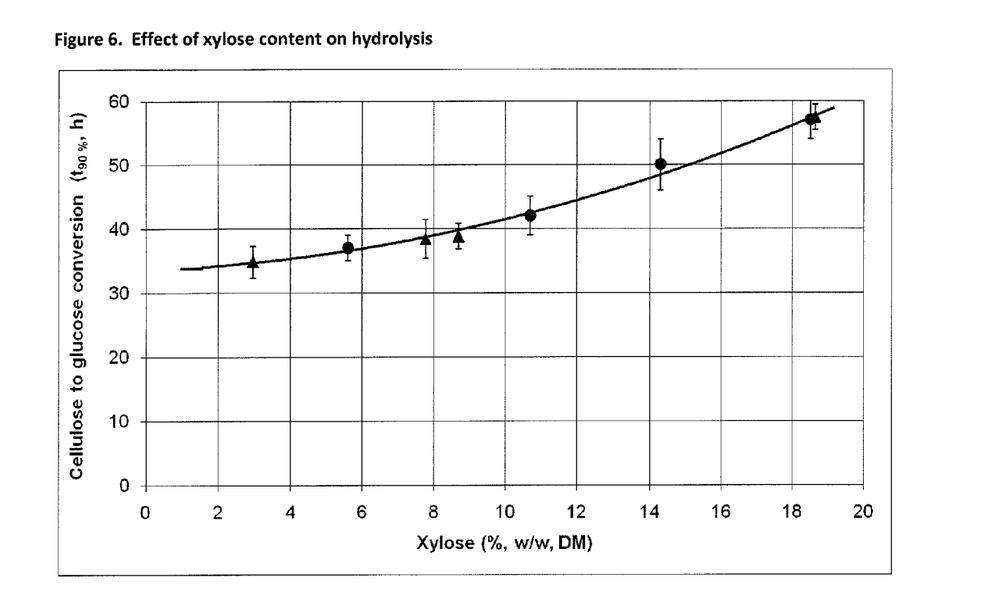
FIG. 6 shows the effect of xylose content on conversion of cellulose to sugar.

FIG. 6 shows that decreasing the xylose content decreased the amount of time needed to achieve cellulose to glucose conversion. This shows that a decreased xylose content in the prehydrolysate leads to an increased cellulose to glucose conversion rate.

$_{90\%}$Although the data shown would indicate that operating the process at the highest severity index possible would result in maximum efficiency of the pretreatment process, it was discovered that higher severity indexes led to higher levels of hemicellulose and cellulose degradation with a concomitant increase in toxic glucose and xylose degradation products such as HMF and furfural. Furthermore, the hydrolysis results showed that a xylose content below 6% (w/w DM) was not desirable, since it did not lead to any further increase in cellulose accessibility. Thus, in order to achieve a level of maximum efficiency of the overall cellulose to ethanol conversion process, the pretreatment conditions must be carefully selected to obviate the need for addition of mineral acid, and minimize hemicellulose and toxic degradation product content in the prehydrolysate.

Acceptable pretreatment conditions for continuous and batch steam explosion pretreatment of corncobs were found to be a temperature of 195-215° C., a pressure of 188 psig to 290 psig and an exposure time of 4 to 10 minutes. Improved results were achieved at temperatures of 203 to 207° C., pressures of 220 psig to 250 psig and exposure times of 7 to 9 minutes. Optimal results were achieved at a temperature of 205° C., a pressure of 235 psig and an exposure time of 8 minutes.

the governing factors for the effectiveness of the steam explosion pretreatment were found to be steam temperature and exposure time. These two factors are combined into a single predictor of the pretreatment process, herein referred to as severity index for the purposes of this description. The severity index is calculated as follows:

$$\text{Severity Index} = \text{Log} \exp[(T-100)/14.75] \times RT$$

Effectiveness of the pretreatment process in accordance with the invention is achieved at a severity index of 3.88 to 4.11. Maximum effectiveness is achieved at a severity index of about 3.995. Pretreatment carried out at severity index greater than 4.30 led to severe degradation of corn cobs prehydrolysate.

The average acetic acid content of corncob prehydrolysate produced by continuous steam explosion pretreatment was lower (2.6+/−0.5% w/w, DM) than that of batch prehydrolysate (3.8%+/−0.3%) although cellulose digestibility (FIG. 2) and fermentability (FIGS. 4A and 4B) of continuous and batch corncob prehydrolysates were similar.

EXAMPLE

Figure 5:
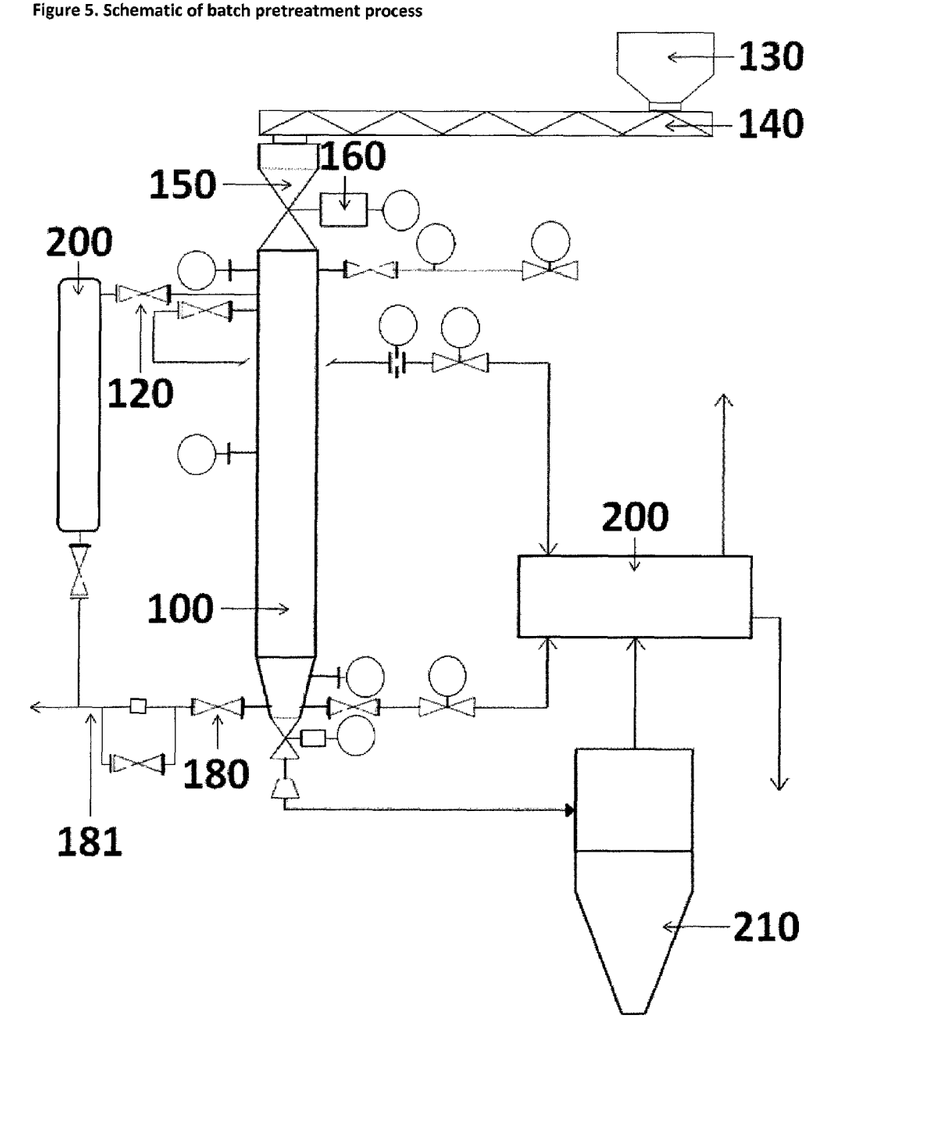
FIG. 5 is a schematic illustration of an experimental cellulose pretreatment system in accordance with the invention.

Batch steam explosion corncob pretreatment was carried out in a steam gun treatment process and experimental cellulose pretreatment setup as shown in FIG. 5. The setup included steam gun 100, supplied with saturated steam from a steam storage vessel 110, through valve 120 and with ground corn cobs of 0.5 to 1 $cm^3$ particle size through a V shaped hopper 130 and screw auger 140 (from Genemco). The amount of each batch load was controlled by a weigh hopper 150. Batch loads of 6 kg corncob DM were used per steam explosion shot. Corncob weight and production rates are expressed on a dry matter basis. After filling the batch load into the steam gun 100 from above, a fill gate 160 was closed to seal the steam gun 100 to ambient. Pressurized saturated steam at temperatures of 190 to 210° C. was fed into the steam gun 100 from steam storage vessel 110, which in turn was supplied with saturated steam from a steam generator (not shown) until the desired cooking pressure was reached. Cooking pressures of 180 psig to 275 psig were used (12.6 to 19.1 bars). Volatiles were continuously vented through the air purge 160 during the first 2 minutes after the desired cooking pressure was reached. Volatiles and condensate were vented sequentially through the liquid purge 170 located at the bottom of the steam gun during the rest of the pretreatment time. After a residence time of 3 to 10 minutes, the pressure in the steam gun was quickly released by opening a flash purge valve 170 located at the bottom of the steam gun. Complete pressure relief was achieved in 600 ms to 1000 ms. During the residence time and prior to pressure release, condensate and cooking liquids collected at the bottom of the steam gun were purged through purge discharge control valve 180 and fed to a condensate hydrolysis station (not shown) through purge conduit 181. Solids and gaseous reaction products ejected from the steam gun 100 on pressure release were separated in a cyclone separator 210. The solids collected at the bottom of cyclone separator 210 were subjected to further processing in the lab. The gaseous components were collected and condensed and fed to the condensate hydrolysis station. Any gaseous emissions from the steam gun, the cyclone separator and other parts of the setup were collected and treated in an environmental control unit 200. Cleaned gases were exhausted to atmosphere from unit 200.

Carbohydrate composition analysis of corncob as fed and corncob prehydrolysates collected at the bottom of the cyclone separator was carried out at Paprican's analytical laboratory (Montreal, Qc) as described above.

Corncob pretreatment screening was performed by enzymatic hydrolysis of low consistency corncob prehydrolysates (10%) using 3.5% (w/w, DM GC220) load of enzyme. Hydrolysis experiments were carried out at 50° C., pH 5.0 in a 1-Liter stirred reaction vessel (150 rpm). pH was adjusted with aqua ammonia (15%, w/w). Enzymatic hydrolysis of 20% corncob hydrolysate produced under optimum pretreatment conditions were carried out at 50° C. using 2.5% load of enzyme. Fermentation of the resulting 20% consistency hydrolysates were carried out at 35° C. using industrial grade commercially available yeast (*Saccharomyces cerevisiae*).

pH adjustment was performed using ammonium hydroxide. A 15% ammonium hydroxide solution was used to maintained hydrolysis pH at pH 5.0. A 30% ammonium hydroxide solution was used to carried out initial pH adjustment of the fermentation.

REFERENCES

1. Wyman, C. 1996. Hemicellulose hydrolyzate conversion. In Handbook on bioethanol: production and utilization. C. Wyman, Editor, Taylor and Francis, Washington D.C. pp 298
2. Badal, C. S. 2003. Hemicellulsoe bioconversion. J. Ind. Microb. Biotechnol. 30/5:279-291

3. Walther, T., P. Hensirisak, F. A. Agblevor. 2001. The influence of aeration and hemicellulose sugars on xylitol production by *Candida tropicalis*. Biores. Technol. 76/3: 213-220.
4. Clarke, A. J. 1996. Chemistry and structure of cellulose and heteroxylan. In Biodegradation of cellulose: Enzymology and Biotechnology. Lancaster, Pa.: Technomic Press, pp 9
5. Torget, R., P. Walter, M. Himmel, K. Grohmann. 1991. Dilute-acid pretreatment of corn residues and short rotation woody crops. Appl. Biochem. Biotechnol. 28/29:75-86
6. Torget, R., P. Walter, M. Himmel, K. Grohmann. 1992. Dilute-acid pretreatment of two short-rotation herbaceous crops. Appl. Biochem. Biotechnol. 34/35:115-123
7. Rydholm, S. A. 1965. Wood chemistry. In Pulping processes. Interscience Publisher, NY. p 95-96
8. Ruzene, D. S., E. Yagiz, D. Marangoz, D. P. Silva, A. A. Vicente, J. A. Teixeira. 2008. Hydrothermal treatments of corn cobs and hemicellulose extraction. In Proceedings of the 10th International Chemical and Biological Engineering Conference, CHEMPOR 2008. E. C. Ferreira and M. Mota eds. Braga, Portugal, Sep. 4-6, 2008
9. Garrote, G., H. Dominguez, J. C. Parajo. 1999. Mild autohydrolysis: an environmentally friendly technology for xylooligosaccharide from wood. J. Chem. Technol. Biotechnol. 74:1101-1109.
10. Vasquez, M. J. J. L. Alonso, H. Dominguez, J. C. Parajo. 2006. Enhancing the potential of oligosaccharides from corncob autohydrolysis as prebiotic food ingredient. Industrial Crops and products. 24:152-159
11. Moura, P., R. Barata, F. Carvalheiro, F. Girio, M. C. Loureiro-Diaz, M. P. Esteves. 2007. In vitro fermentation of xylo-oligosaccharides from corn cobs autohydrolysis by *Bifidobacterium* and *Lactobacillus* strains. LWT. 40:963-972.
12. Garrote, G., H. Dominguez, J. C. Parajo. 2001. Kinetic modelling of corncob autohydrolysis. Proc. Biochem. 36: 571-578
13. Garrote, G., H. Dominguez, J. C. Parajo. 2002. Autohydrolysis of corncob: study of non-isothermal operation for xylooligosaccharide production. J. Food. Eng. 52: 211-218.
14. Aoyama, M. 1996. Steaming pretreatment of bamboo grass. II. Characterization of solubilised hemicellulose and enzymatic digestibility of water extracted residue. Cellulose Chemistry and Technology. 30:385-393.
15. Carvalheiro. F., M. P. Esteves, J. C. Parajo, H. Peirera, F. M. Girio. 2004. Production of oligosaccharides by autohydrolysis of brewery's spent grain. Bioressource Technology. 91: 93-100.
16. Gans, I., D. Potts, A. Matsuo, T. Tse, M. Holysh, P. Assarsson. 1989. Process development for plug flow acid hydrolysis and conversion of lignocellulosics to ethanol. In Bioenergy: Proc 7th Can. Bioenergy R&D Semina, E. Hogan, ed., NRC Canada, pp. 419-423.
17. Lawford, H. G., J. D. Rousseau. 1992. Effect of acetic acid on xylose conversion to ethanol by genetically engineered *E. coli*. Appl. Biochem. Biotechnol. 34/35:185-204
18. Ferrari, M. D., E. Neirotti, C. Albornoz, E. Saucedo. 1992. Ethanol production from Eucalyptus wood hemicellulose hydrolyzate by *Pichia stipitis*. Biotech. Bioeng. 40:40753-759.
19. Lawford, H. G., J. D. Rousseau. 1993. Effect of pH and acetic acid on glucose and xylose metabolism by a genetically engineered ethanologenic *Escherichia coli*. Appl. Biochem. Biotechnol. 39/40:301-322
20. McMillan, J. D. 1994. Conversion of hemicellulose hydrolyzates. In Bioconversion for fuels. M. E. Himmel, J. O. Baker and R. P. Overend, eds., ACS Symposium Seried 566, American chemical Society, pp. 411-437.
21. Narendranath, N. V. K. C. Thomas. W. M. Ingledew. 2001. Acetic acid and lactic acid inhibition of growth of *Saccharomyces cerevisiae* by different mechanisms. J. Am. Soc. Brew. Chem. 59:187.
22. Narendranath, N. V. K. C. Thomas. W. M. Ingledew. 2001. Effects of acetic acid and lactic acid on the growth of *Saccharomyces cerevisiae* in a minimal medium. Journal of industrial microbiology and Biotechnology. 26/3: 171-177.
23. Kuyper, M., A. A. Winkler, J. P. Van Dijken, J. T. Pronk. 2004. Minimal metabolic engineering of *Saccharomyces cerevisiae* of efficient anaerobic xylose fermentation: a proof of principle. FEMS Yeast Res. 4: 655-664
24. Krisch, J., B. Scajani. 1997. Ethanol and acetic acid tolerance in free and immobilized cells of *Saccharomyces cerevisiae* and *Acetobacter aceti*. Biotechnology Letter. 19/6: 525-528.
25. Pampulha, M. E. and Loureiro-Dias, M. C. (1990) Activity of glyco-lytic enzymes of *Saccharomyces cerevisiae* in the presence of acetic acid. Appl. Microbiol. Biotechnol. 34/3:375-380.
26. Thomas, K. C. S. H. Hynes, W. M. Ingledew. 2002. Influence of medium buffering capacity on inhibition of *Saccharomyces cerevisiae* growth by acetic acid and lactic acids. Appl. Environ. Microbiol. 68/4:1616-1623.
27. Graves, T., N. V. Narendranath, K. Dawson, R. Power. 2006. Effects of lactic or acetic acid on ethanol productivity by *Saccharomyces cerevisiae* in corn mash. Appl. Microbiol. Biotechnol. 33/6:469-474.

What is claimed is:

1. A process for the pretreatment of corncob biomass for biofuel production by fermentation, comprising the steps of exposing corncob to steam in a reaction vessel at an elevated temperature and reaction pressure for a preselected exposure time, venting volatile compounds continuously over the pretreatment time and releasing the reaction pressure for explosive decomposition of the corncob biomass into a fibrous solids portion and a condensate portion, wherein the exposing step is carried out at a temperature of 190° C.-210° C. and a pressure of 190 psig to 275 psig and an exposure time of 3 to 10 minutes for minimizing the acetic content in the fibrous solids portion.

2. A process for the pretreatment of corncob biomass for biofuel production by fermentation, comprising the steps of exposing corncob to steam in a reaction vessel at an elevated temperature and reaction pressure for a preselected exposure time, venting volatile compounds continuously over the pretreatment time and releasing the reaction pressure for explosive decomposition of the corncob biomass into a fibrous solids portion and condensate, wherein the exposing step is carried out at a temperature of 203-207° C. and a pressure of 220-250 psig and an exposure time of 7-9 minutes for minimizing acetic acid content in the fibrous solids portion.

3. The process of claim 2, further comprising the steps of separately capturing the condensate and the solids generated during the pressure release and removing the captured condensate.

4. The process of claim 2, comprising the further step of collecting condensate and liquid reaction products in the reaction vessel during the exposure time and removing the collected reaction products from the reaction vessel prior to the pressure release.

5. A process for the pretreatment of corncob biomass for biofuel production by fermentation, comprising the steps of exposing corncob to steam in a reaction vessel at an elevated temperature and reaction pressure for a preselected exposure time, venting volatile compounds continuously over the pretreatment time and releasing the reaction pressure for explosive decomposition of the corncob biomass into a fibrous solids portion and condensate, wherein the exposing step is carried out at a temperature of 205° C., a pressure of 235 psig and for a time interval of 8 minutes for minimizing acetic acid content in the fibrous solids portion.

6. The process of claim 5, wherein the pressure is released within less than 1000 milliseconds.

7. The process of claim 6, wherein the pressure is released within 300 milliseconds.

8. A process for the pretreatment of corncob biomass, comprising the steps of exposing corncob to steam in a reaction vessel at an elevated temperature and reaction pressure for a preselected exposure time, venting volatiles and releasing the reaction pressure for explosive decomposition of the corncob biomass into fibrous solids and condensate, the process conditions being selected for the achievement of a severity index of 3.88 to 4.11.

9. The process of claim 8, comprising the further step of collecting condensate and liquid reaction products in the reaction vessel during the exposure time and removing the collected reaction products from the reaction vessel prior to the pressure release.

10. The process of claim 8, wherein the process conditions are selected for the achievement of a severity index of 4.0.

* * * * *